(12) United States Patent
Hess et al.

(10) Patent No.: US 9,638,700 B2
(45) Date of Patent: May 2, 2017

(54) NT-PRO ANP AND SFLT-1 FOR THE DIFFERENTIATION BETWEEN CIRCULATORY AND ISCHEMIC EVENTS

(75) Inventors: Georg Hess, Mainz (DE); Dietmar Zdunek, Tutzing (DE); Andrea Horsch, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/461,833

(22) Filed: May 2, 2012

(65) Prior Publication Data

US 2012/0214180 A1  Aug. 23, 2012

Related U.S. Application Data

(63) Continuation of application No. PCT/EP2010/066660, filed on Nov. 2, 2010.

(30) Foreign Application Priority Data

Nov. 3, 2009 (EP) .................................... 09174873

(51) Int. Cl.
  *G01N 33/53* (2006.01)
  *G01N 33/68* (2006.01)

(52) U.S. Cl.
  CPC ..... *G01N 33/6893* (2013.01); *G01N 2333/58* (2013.01); *G01N 2333/71* (2013.01); *G01N 2800/32* (2013.01); *G01N 2800/347* (2013.01)

(58) Field of Classification Search
  None
  See application file for complete search history.

(56) References Cited

U.S. PATENT DOCUMENTS

| 5,744,305 A | 4/1998 | Fodor et al. |
| 2006/0008829 A1 | 1/2006 | Hess et al. |
| 2007/0269836 A1 | 11/2007 | McPherson et al. |
| 2009/0155827 A1 | 6/2009 | Zeiher et al. |

FOREIGN PATENT DOCUMENTS

| EP | 1903339 A1 | 3/2008 |
| WO | 2007/028070 A3 | 3/2007 |

OTHER PUBLICATIONS

Bonow, Robert O., "New Insights Into the Cardiac Natriuretic Peptides," Circulation, 1996, pp. 1946-1950, vol. 93.
Hanley, James A. and McNeil, Barbara J., "The Meaning and Use of the Area under a Receiver Operating Characteristic (ROC) Curve," Radiology, Apr. 1982, pp. 29-36, vol. 143.
Nolan, John P. and Sklar, Larry A., "Suspension array technology: evolution of the flat-array paradigm," Trends in Biotechnology, Jan. 2002, pp. 9-12, vol. 20, No. 1.
Reinecke, et al., "Dilemas in the Management of Atrial Fibrillation in Chronic Kidney Disease", J. Am. Soc. Nephrol., 20:705-711 (2009).
Schlaich, et al., "Sympathetic Activation in Chronic Renal Failure", J. Am. Soc. Nephrol., 20:933-939 (2009).

*Primary Examiner* — Marianne P Allen
(74) *Attorney, Agent, or Firm* — McDonnell Boehnen Hulbert & Berghoff LLP

(57) ABSTRACT

The present disclosure relates to the field of laboratory diagnostics. The present disclosure provides means and methods for differentiating between an acute circulatory event and an ischemic event, as the cause underlying an acute medical event of a patient.

3 Claims, No Drawings

NT-PRO ANP AND SFLT-1 FOR THE DIFFERENTIATION BETWEEN CIRCULATORY AND ISCHEMIC EVENTS

PRIORITY CLAIM

This application is a continuation of International Application No. PCT/EP2010/066660, filed Nov. 2, 2010, which claims the benefit of European Patent Application No. 09174873.1, filed Nov. 3, 2009, the disclosures of which are hereby incorporated by reference in their entirety.

FIELD OF THE DISCLOSURE

The present disclosure relates to the field of medical diagnostics. More specifically, the present disclosure relates to diagnostic applications, and systems for performing the same, which may be used in the diagnosis of one or more causes underlying an acute medical event of a patient.

BACKGROUND OF THE DISCLOSURE

Patients in emergency units or emergency departments of hospitals often present with suddenly developing, potentially life threatening conditions. The extent and the duration of said conditions are frequently unknown. The first steps of therapy are generally, and necessarily, directed at the support of the patient's vital functions such as mechanical ventilation, fluid supply, blood transfusion, defibrillation, external pacing or pharmacotherapy (for example, the administering epinephrine or vasopressin for low blood pressure; administering amiodarone, lidocaine, procainamide or magnesia sulphate for ventricular fibrillation; administering epinephrine, atropine or sodium bicarbonate for asystole). However, in most cases the impaired vital functions are only the symptom of another pre-existing condition. A successful therapy of the patient, thus, requires treatment of the cause underlying the acute condition. In cases of trauma the cause may be obvious. In other cases it may be more difficult to find.

In many cases, the underlying causes of a patient's symptoms (which may be life-threatening) are not readily apparent. For example, dyspnea can be caused by such diverse conditions as heart failure, pneumonia, sepsis, acute respiratory distress syndrome and pulmonary embolism. Syncope, the transient loss of consciousness and postural tone, may occur suddenly without warning or may be preceded by symptoms such as lightheadedness, dizziness, a feeling of warmth, nausea, diaphoresis and visual blurring. The ability of medical professionals to differentiate between syncope and seizure, for example, is important and in some cases difficult.

A pathophysiological mechanism underlying syncope is vasal dysregulation. Vasal dysregulation can have a variety of causes. For example, cardial causes include pulmonary embolism, acute myocardial infarction, cardiac arrhythmias (bradyarrhythmias as well as tachyarrhythmias) or hypertrophic obstructive cardiomyopathy. Syncope can also be caused by the activation of the parasympathetic nervous system which may be triggered by events such as painful or unpleasant stimuli, prolonged standing, rapid change from a reclining into an upright position, hyperthermia or urination. Another unspecific symptom that may be associated with life threatening conditions is acute chest discomfort. This symptom can be caused by stable angina, acute cardiovascular events (unstable angina or myocardial infarction), pulmonary embolism, peptic ulcer or pneumonia, for example.

Differential diagnosis takes into account the history of the patient and includes a clinical examination. These procedures may be time consuming and the administration of analgetics may reduce the diagnostic value of a clinical examination. Moreover, it is difficult or impossible to get information on history of the patient if the patient suffers from reduced consciousness or is mechanically ventilated. However, a rapid diagnosis allows a rapid initiation of a suitable therapy, reduces the suffering of the patient and increases his/her chances of survival.

Clinically, ischemic events (such as those described above) are characterized by pain, paleness of the skin, and weak or absent pulse in the affected area. Additionally, imaging methods may be used for the characterization of ischemic events, such as ultrasonography, computed tomography, magnetic resonance imaging (with and without contrast agent), angiography and scintigraphy may be used.

Circulatory complications may be detected by the presence of abnormal blood pressure. Occasionally, the presence of cardiac arrhythmia and acute cardiovascular events may be used as an additional indicator for circulatory complications. However, these and other known methods for detecting circulatory events do not allow for the diagnosis of temporary complications. Moreover, the methods known in the art do not yield quantitative information about the severity of a circulatory complication.

Symptoms and complications associated with ischemic events, for example, may be diagnosed with an initial evaluation of chest-pain patients including an electrocardiogram (ECG) and cardiac markers such as troponins. These tests, while specific, may be insensitive and can leave the requirement for further testing to achieve an accurate diagnosis. Other methods of diagnosis include magnetocardiography imaging which utilizes superconducting quantum interference devices to detect the weak magnetic fields generated by the heart's electrical fields (which utilizes the correlation between abnormal cardiac depolarisation or repolarisation and abnormality in the magnetic field map). Magnetocardiography imaging is approved by the Food and Drug Administration (FDA) as a safe device for the non-invasive detection of ischemia. However, in general these methods are generally, complicated, slow and not very sensitive.

SUMMARY OF THE DISCLOSURE

The present disclosure provides means and methods to differentiate between an acute circulatory event and an ischemic event as the cause underlying an acute medical event of a patient.

According an embodiment of the disclosure, a method for rapidly diagnosing if an acute medical event in an emergency patient is associated with a circulatory and/or an ischemic complication is provided. The method comprises the steps of: a) determining the amount of an ANP-type peptide in a sample of a patient; b) determining the amount of sFlt-1 in a sample from a patient; c) comparing the amounts measured in steps a) and b) to reference amounts; and establishing a diagnosis based on the results of c), and d) establishing a diagnosis based on the results of c), wherein an increased level of the ANP-type peptide relative to the reference amount is indicative of a circulatory complication and wherein an increased level of sFlt-1 relative to the reference amount is indicative of an ischemic complication, wherein the circulatory complication is caused by cardiac arrhythmia, and wherein the ischemic complication is characterized by a systolic blood pressure of less than 80 mmHg.

According to some embodiments, increased levels of sFlt-1 and the ANP-type peptide relative to the reference amounts are indicative of a combined circulatory and ischemic complication.

In some embodiments, a method for diagnosing one of a circulatory complication and an ischemic complication associated with an acute medical event in a subject is provided. The method includes the steps of contacting, in vitro, a portion of a sample from a subject with an antibody immunoreactive for an ANP-type peptide; contacting, in vitro, a portion of the sample from the subject with an antibody immunoreactive for a sFlt-1 peptide; determining the amounts of the ANP-type peptide and the sFlt-1 peptide in the sample based on said steps of contacting. The method also includes the steps of comparing the amounts of the ANP-type peptide and the sFlt-1 peptide (determined in the steps of determining) with reference amounts for ANP-type peptide and sFlt-1 peptide, respectively. Such methods also include the steps of diagnosing one of a circulatory complication if the amount of ANP-type peptide determined in said step of determining is greater than the reference amount for ANP-type peptide and an ischemic complication if the amount of sFlt-1 peptide determined in said step of determining is greater than the reference amount for sFlt-1 peptide.

In some embodiments, the ANP-type peptide is NT-proANP or a variant thereof. In some such embodiments, the reference amount for NT-proANP is about 2500 pg/ml.

According to some embodiments, the reference amount for sFlt-1 is about 500 pg/ml.

According to other embodiments of the disclosure, a system for diagnosing one of a circulatory complication or an ischemic complication associated with an acute medical event in a subject is provided. According to some such embodiments, the system includes an analyzing unit comprising means for contacting, in vitro, a portion of a sample from a subject with an antibody immunoreactive for an ANP-type peptide and means for determining the amount of the ANP-type peptide in the sample and an analyzing unit comprising means for contacting, in vitro, a portion of the sample from the subject with an antibody immunoreactive for an sFlt-1 peptide and means for determining the amount of the sFlt-1 peptide in the sample. The system also includes a computing device having a processor and a non-transient machine readable media including a plurality of instructions executable by the processor, the instructions, when executed compare the amount of ANP-type peptide determined by the analysing unit comprising means for determining the amount of ANP-type peptide to a reference amount of ANP-type peptide, compare the amount of sFlt-1 peptide determined by the analysing unit comprising means for determining the amount of sFlt-1 peptide to a reference amount of sFlt-1 peptide, provide a diagnosis of a circulatory complication if the amount of ANP-type peptide in the sample is greater than the reference amount for ANP-type peptide, and provide a diagnosis of an ischemic complication if the amount of sFlt-1 peptide in the sample is greater than the reference amount for sFlt-1 peptide.

In yet other embodiments of the instant disclosure, a kit for facilitating a diagnosis of one of a circulatory complication and an ischemic complication associated with an acute medical event in a subject is provided. Some embodiments of such a kit include a first antibody with specific binding affinity to an ANP-type peptide or a variant thereof, a first antibody with specific binding affinity to a sFlt-1 peptide or a variant thereof, a second antibody with specific binding affinity to a portion of the ANP-type peptide or a variant thereof different than the first antibody with specific binding affinity to the ANP-type peptide or variant thereof, the second antibody having a reporting molecule linked thereto, and a second antibody with specific binding affinity to a portion of the sFlt-1 peptide or a variant thereof different than the first antibody with specific binding affinity to the sFlt-1 peptide or variant thereof, the second antibody having a reporting molecule linked thereto. Additionally, in some embodiments of a kit according to the instant disclosure, literature is provided. The literature may include reference amount for ANP-type peptide, a reference amount for sFlt-1 peptide, a diagnosis of a circulatory complication if a measured amount of ANP-type peptide in a sample of the subject, determined using the first and second antibody with specific binding affinity to the ANP-type peptide, is greater than the reference amount for ANP-type peptide, and a diagnosis of an ischemic complication if the amount of sFlt-1 peptide in the sample of the subject, determined using the first and second antibody with specific binding affinity to the sFlt-1 peptide, is greater than the reference amount for sFlt-1 peptide.

According to some embodiments of the kits disclosed herein, the first antibody with specific binding affinity to the ANP-type peptide is immobilized.

In yet some further embodiments of kits disclosed herein, a first reference standard having the reference amount for ANP-type peptide; and a second reference standard having the reference amount for sFlt-1 peptide are also provided.

DETAILED DESCRIPTION OF THE EMBODIMENTS OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

According to the present disclosure, a system and method for a rapid diagnostic test which can be used at the point of care to aid diagnosis of the causes underlying critically reduced vital functions in a patient is provided. The system and methods provided herein surprisingly and unexpectedly provide for diagnosing if an acute medical event in an emergency patient is associated with a circulatory and/or an ischemic complication. The instant disclosure also provides devices and kits for utilizing the system and methods disclosed herein.

According to some embodiments of the present disclosure, a method for rapidly diagnosing if an acute medical event in an emergency patient is associated with a circulatory and/or an ischemic complication is provided. In some embodiments, the method includes the steps of:
  a) determining the amount of an ANP-type peptide in a sample of a patient;
  b) determining the amount of sFlt-1 in a sample from a patient;
  c) comparing the amounts measured in steps a) and b) to reference amounts; and
  d) establishing a diagnosis based on the results of c).

The term "acute medical event" refers to a condition of a patient which induces or causes the patient to seek medical assistance. For example, the condition may be a serious, potentially life threatening condition such as a failure of one or more vital body functions or a relatively non-serious condition. A failure of one or more vital body functions may refer to the sudden failure of organs whose functions (or function) are essential for survival. Also the term may be used to refer to the sudden deterioration of a previously stable condition. Exemplary organs whose functions are essential for survival include the lung, the heart, (at least one of) the kidneys and the liver. Consequences of organ failure depend on the organ in question. Signs of organ failure depend on the affected organ and may include, pain, metabolic acidosis, anuria, hepatic encephalopathy, insufficient oxygenation of the blood and loss of consciousness. However, the diagnosis of organ failure on its own does not give enough indication of a suitable therapy.

The term "circulatory complication," as used herein, may refer to a sudden deterioration of the function of the heart. Such deterioration may be caused by cardiac arrhythmia, transient cardiac arrest or pulmonary embolism, for example. Cardiac arrhythmia can occur in two forms: bradyarrhythmia and tachyarrhythmia. In bradyarrhythmia the frequency of heartbeat is pathologically decreased in comparison to a healthy subject, for example in bradyarrhythmia the heart rate is likely lower than about 60 beats per minute. The most frequent forms of bradyarrhythmia include sinus bradycardia, sinoatrial block, sinus arrest, sick sinus syndrome and atriventricular block. In tachyarrhythmia the frequency is pathologically increased when compared with a healthy subject, for example in tachyarrhythmia the heart rate is likely higher than about 100 beats per minute. Most cases of tachyarrhythmia include at least one of supraventricular tachycardia (associated with structural cardiovascular disease), atrial fibrillation (associated with Wolff-Parkinson-White syndrome), atrial flutter (associated with 1:1 atrioventricular conduction), and ventricular tachycardia. Pulmonary embolism may be caused by the occlusion of a pulmonary artery by a blood clot (thromboembolism) or an air bubble (air embolism). In some instances, blood clots may be formed in the pelvic or lower extremity veins and migrate to the pulmonary arteries where they get occlude an artery (or arteriole or the like). An air embolism may be caused by a diving accident or by leaky venous catheters, for example. Symptoms of pulmonary embolism include chest pain, dyspnea and hemoptysis (coughing of blood). The pressure in the lung circulation may rise and may cause right ventricular failure.

The term "ischemic complication," as used herein may, refer to a suddenly occurring hypoxia in any tissue or organ. For example, the term may refer to ischemia of the spleen, bowel, kidney, heart or one or more limbs. Acute ischemia may be caused by the formation of blood clots in an artery of the systemic circulation. The parts of the organ that rely on the occluded artery for their blood supply may then be (at least partially) cut off from their needed blood supply. Decreased blood pressure is another frequent cause of ischemia. Depending on the duration of ischemia, the oxygen demand of the ischemic tissue and the remaining blood supply, the affected tissue may begin to die by necrosis (and eventually die by necrosis). An ischemic complication as referred to herein may be characterized by a systolic blood pressure of less than 80 mmHg. Moreover, the ischemic complication may also be characterized by organ specific pain, a reduced pulse in the affected area and/or paleness of the skin.

An acute medical event, as used herein, may be associated with circulatory and/or ischemic complications if such complications precede or accompany the acute medical event, for example. If such complications precede the acute medical event they may take place 1, 2, 3 or 4 hours before the patient seeks medical assistance. Thus, in some instances, the acute medical event may actually be caused by (or enhanced by) such complications.

The term "diagnosing if an acute medical event in an emergency patient is associated with a circulatory and/or an ischemic complication" as used herein refers to identifying the pathophysiological disorder or condition accompanying or preceding the acute medical event from which the patient is suffering or which was diagnosed when the patient presented in the hospital or emergency unit. As will be understood by those skilled in the art, such an assessment is usually not intended to be correct for 100% of the subjects to be diagnosed. The term, however, intends that a statistically significant portion of subjects can be correctly diagnosed to suffer from the disease or condition. Whether a portion is statistically significant can be determined by a person skilled in the art using various well known statistic evaluation tools including, for example determination of confidence intervals, p-value determination, Student's t-test, Mann-Whitney test, etc. Details may be found in Dowdy and Wearden, Statistics for Research, John Wiley & Sons, New York 1983. According to the instant disclosure, exemplary confidence intervals include at least approximately 90%, at least approximately 95%, at least approximately 97%, at least approximately 98% or at least approximately 99%, for example. The p-values, according to the instant disclosure, may include approximately 0.1, 0.05, 0.01, 0.005, or 0.0001, for example. Additionally, the probability envisaged by the present disclosure allows that a diagnosis will be correct for at least approximately 60%, at least approximately 70%, at least approximately 80%, or at least approximately 90% of the subjects of a given cohort or population.

According to some embodiments of the present disclosure, a diagnosis that the patient has suffered an ischemic and/or circulatory complication is indicative of the patient suffering from a severe, potentially life threatening condition and requires close medical attention.

An assessment according to methods disclosed herein, includes a rapid assessment. A rapid assessment may be performed at the point of care. Results of an assessment may be available in less than about 120 minutes, and in some cases even less than about 60 or even about 30 minutes after admission of the patient to the emergency unit (or admission to the emergency ambulance or after the first physician or medical personal was consulted, for example). In some instances, an assessment may be available in less than about 60 minutes after the patient first seeks medical assistance, for example.

According to some embodiments of the instant disclosure, methods disclosed herein may be practised in an emergency unit. As used herein, the term "emergency unit" may refer to any location where individuals/patients with a (real or suspected) medical emergency condition consult a person having a medical background, for example a physician, to have an analysis of their pathological state and the cause underlying their condition. Typical examples include emergency departments or emergency rooms in hospitals, emergency ambulances, doctor's offices and other institutions suitable for treatment of patients.

An "emergency patient" may be a patient presenting to an emergency unit or a patient who, from the perspective of a physician—based on the patient's symptoms and medical history, should present to an emergency unit.

According to the instant disclosure, some embodiments of the methods disclosed herein include in vitro methods. For example, the determination of the respective peptide (an ANP-type peptide or sFlt-1) or peptides to be determined may be carried out in vitro.

Additionally, methods disclosed herein may be used in combination with other diagnostic methods. A person of skill in the art will understand that a differential diagnosis may require a combination of the patient's history, a clinical examination, and laboratory tests. Further, according to some embodiments, the methods of the present disclosure may be applied to guide the further examination of a patient and to exclude unnecessary tests.

In some embodiments of the instant disclosure, further examination of the patient may utilize imaging methods. Ultrasonography, computed tomography, magnetic resonance imaging (with and without contrast agent), angiography and scintigraphy are some such exemplary imaging methods.

The term "ANP-type peptide" refers to ANP, proANP, pre-proANP and NT-proANP. ANP is synthesized and secreted by the atria. Mature ANP is generated by sequential cleavage of pre-proANP comprising 151 amino acids. Cleavage of a signal peptide (25 amino acids) gives proANP (126 amino acids). Upon secretion the propeptide is split into the biologically active ANP (28 amino acids and the inactive N-terminal moiety (98 amino acids). The turnover of ANP is rapid as its half-life is only 2.5 minutes in blood. ANP promotes systemic arterial dilation, natriuresis, diuresis and renin inhibition, blood pressure is, thus, decreased by the action of ANP (see for example, Bonow, 1996, Circulation 93: 1946-1950).

The term "soluble Flt-1" or "sFlt-1" as used herein refers to a polypeptide which comprises a soluble form of the VEGF receptor Flt1. It was identified in conditioned culture medium of human umbilical vein endothelial cells. The endogenous soluble Flt1 (sFlt1) receptor is chromatographically and immunologically similar to recombinant human sFlt1 and binds [125I] VEGF with a comparable high affinity. Human sFlt1 is shown to form a VEGF-stabilized complex with the extracellular domain of KDR/Flk-1 in vitro. sFlt1 may refer to human sFlt1, for example, such as human sFlt1 deduced from the amino acid sequence of Flt-1 as shown in Genebank accession number P17948, GI: 125361. An amino acid sequence for mouse sFlt1 is shown in Genebank accession number BAA24499.1, GI: 2809071.

The terms "ANP-type peptide" and "sFlt-1" used herein also encompass variants of the aforementioned ANP-type or sFlt-1 polypeptides. Such variants have at least the same essential biological and immunological properties as the specific ANP-type or sFlt-1 polypeptides. In particular, they share the same essential biological and immunological properties, for example, if they are detectable by the same specific assays referred to in this specification, e.g., by ELISA assays using polyclonal or monoclonal antibodies specifically recognizing the said ANP-type or sFlt-1 polypeptides. Moreover, it is to be understood that a variant as referred to in accordance with the present disclosure shall have an amino acid sequence which differs due to at least one amino acid substitution, deletion and/or addition wherein the amino acid sequence of the variant is still at least 50%, 60%, 70%, 80%, 85%, 90%, 92%, 95%, 97%, 98%, or 99% identical with the amino sequence of the specific ANP-type or sFlt-1 polypeptide, over the entire length of the specific ANP-type peptide (e.g. human ANP, human proANP, human NTproANP) or of the specific human sFlt-1, respectively. The degree of identity between two amino acid sequences can be determined by algorithms well known in the art. The degree of identity may be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage may be calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT may be employed to determine their optimal alignment and, thus, the degree of identity. Preferably, the default values of 5.00 for gap weight and 0.30 for gap weight length may be used. Variants referred to above may be allelic variants or any other species specific homologs, paralogs, or orthologs. Moreover, the variants referred to herein include fragments or subunits of the specific ANP-type or sFlt-1 polypeptides or the aforementioned types of variants as long as these fragments have the essential immunological and biological properties as referred to above. Such fragments may be, e.g., degradation products of the ANP-type or sFlt-1 peptides. Further included are variants which differ due to posttranslational modifications such as phosphorylation or myristylation.

Determining the amount of an ANP-type peptide or sFlt-1 or any other peptide or polypeptide referred to in this specification relates to measuring the amount or concentration, for example as semi-quantitatively or quantitatively. Measuring can be done directly or indirectly. Direct measuring, in general, relates to measuring the amount or concentration of the peptide or polypeptide based on a signal which is obtained from the peptide or polypeptide itself and the intensity of which directly correlates with the number of molecules of the peptide present in the sample. Such a signal—sometimes referred to herein as an intensity signal—may be obtained, by measuring an intensity value of a specific physical or chemical property of the peptide or polypeptide. Indirect measuring includes measuring of a signal obtained from a secondary component (i.e. a component not being the peptide or polypeptide itself) or a biological read out system, for example, including measurable cellular responses, ligands, labels, or enzymatic reaction products.

In accordance with the present invention, determining the amount of a peptide or polypeptide can be achieved by any known means for determining the amount of a peptide in a sample. Such means may comprise immunoassay devices and methods which utilize labelled molecules in various sandwich, competition, or other assay formats. Such assays may develop a signal which is indicative of the presence or absence of the peptide or polypeptide. Moreover, the signal strength can be correlated directly or indirectly (e.g., reverse or proportional) to the amount of polypeptide present in a sample. Further suitable methods comprise measuring a physical or chemical property specific for the peptide or polypeptide such as its precise molecular mass or NMR spectrum. Such methods may comprise biosensors, optical devices coupled to immunoassays, biochips, analytical devices such as mass-spectrometers, NMR-analyzers, or chromatography devices. Further, methods may include micro-plate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

Determining the amount of a peptide or polypeptide may comprise the steps of (a) contacting a cell capable of eliciting a cellular response the intensity of which is indicative of the amount of the peptide or polypeptide with the said peptide or polypeptide for an adequate period of time, and (b) measuring the cellular response. For measuring cellular responses, the sample or processed sample may be added to a cell culture and an internal or external cellular response may be measured. The cellular response may include the measurable expression of a reporter gene or the secretion of a substance such as a peptide, polypeptide, or a small molecule. The expression or substance shall generate an intensity signal which correlates to the amount of the peptide or polypeptide.

According to the embodiments of the instant disclosure, determining the amount of a peptide or polypeptide may comprise the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Additionally, according to some embodiments, determining the amount of a peptide or polypeptide may comprise the steps of (a) contacting the peptide with a specific ligand, (b) (optionally) removing non-bound ligand, and (c) measuring the amount of bound ligand. In some such embodiments, the bound ligand generates an intensity signal. Binding may include both covalent and non-covalent binding. A ligand according to the present invention can be any compound including, for example, a peptide, polypeptide, nucleic acid, or small molecule, binding to the peptide or polypeptide described herein. Exemplary ligands include antibodies, nucleic acids, peptides or polypeptides such as receptors or binding partners for the peptide or polypeptide and fragments thereof comprising the binding domains for the peptides, and aptamers, for example nucleic acid or peptide aptamers. Methods to prepare such ligands may include any method as is known in the art. For example, identification and production of suitable antibodies or aptamers may also include services offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab and F(ab)$_2$ fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids may be prepared any method known in the art. According to embodiments of the present disclosure, the ligand or agent binds specifically to the peptide or polypeptide. Specific binding according to the present invention means that the ligand or agent should not bind substantially to ("cross-react" with) another peptide, polypeptide or substance present in the sample to be analyzed. According to various embodiments of the instant disclosure, the specifically bound peptide or polypeptide should be bound with at least about 3 times higher, at least about 10 times higher or even at least about 50 times higher affinity than any other relevant peptide or polypeptide. Non-specific binding may be tolerable, if it can still be distinguished and measured unequivocally, for example, according to its size on a Western Blot, or by its relatively higher abundance in the sample. Binding of the ligand can be measured by any method known in the art. In some embodiments, the method disclosed herein is semi-quantitative or quantitative. Exemplary methods are described in the following.

First, according to embodiments of the instant disclosure, binding of a ligand may be measured directly, for example, by NMR or surface plasmon resonance.

Next, if the ligand serves as a substrate of an enzymatic activity of the peptide or polypeptide of interest, an enzymatic reaction product may be measured (e.g., the amount of a protease can be measured by measuring the amount of cleaved substrate on a Western Blot for example). According to some embodiments, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal. For measurements of enzymatic reaction products, the amount of substrate may be saturating. The substrate may also be labeled with a detectable label prior to the reaction. In some embodiments, the sample may be contacted with the substrate for an adequate period of time. As used herein, an adequate period of time includes the time necessary for an detectable amount of product to be produced. According to some embodiments, instead of measuring the amount of product, the time necessary for appearance of a given (detectable) amount of product can be measured.

Next, in some embodiments, the ligand may be coupled covalently or non-covalently to a label allowing detection and measurement of the ligand. Labelling may be done by direct or indirect methods. Direct labeling involves coupling of the label directly (covalently or non-covalently) to the ligand. Indirect labeling involves binding (covalently or non-covalently) of a secondary ligand to the first ligand. In some embodiments, the secondary ligand specifically binds to the first ligand. The secondary ligand may be coupled with a suitable label and/or be the target (receptor) of tertiary ligand binding to the secondary ligand. The use of secondary, tertiary or even higher order ligands may be used to increase the signal. Exemplary secondary and higher order ligands may include antibodies, secondary antibodies, and a streptavidin-biotin system (for example, from Vector Laboratories, Inc.). The ligand or substrate may also be "tagged" with one or more tags as known in the art. Such tags may then be targets for higher order ligands. Exemplary tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag may be at (or in proximity to) the N-terminus and/or C-terminus. Exemplary labels include labels detectable by an appropriate detection method. Exemplary labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels are also within the scope of the instant disclosure, and exemplary enzymatically active labels include horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, for example as ready-made stock solution from Roche Diagnostics), CDP-Star™ (for example as available from Amersham Biosciences), ECF™ (for example as available from Amersham Biosciences). A suitable enzyme-substrate combination may result in a colored reaction product, fluorescence or chemoluminescence, which can be measured according to various methods known in the art such as using a light-sensitive film or a suitable camera system). As for measuring the enzymatic reaction, the various methods given above apply analogously. Exemplary fluorescent labels include fluorescent proteins (such as GFP and its derivatives), Cy3, Cy5, Texas Red, Fluorescein, and the Alexa dyes (e.g. Alexa 568). Additionally, further fluorescent labels are available, for example, from Molecular Probes (for example as available from Oregon). Also the use of quantum dots as fluorescent labels is contemplated. Exemplary radioactive labels include $^{35}S$, $^{125}I$, $^{32}P$, $^{33}P$ and the like. A radioactive label may be detected by any method known including, for example, a light-sensitive film or a phosphor imager. Exemplary measurement methods according the present invention also include precipitation (e.g., immunoprecipitation), electrochemiluminescence (e.g., electro-generated chemiluminescence), RIA (e.g., radioimmunoassay), ELISA (e.g., enzyme-linked immunosorbent assay), sandwich enzyme immune tests, electrochemiluminescence sandwich immunoassays (e.g., ECLIA), dissociation-enhanced lanthanide fluoro immuno assay (e.g., DELFIA), scintillation proximity assay (e.g., SPA), turbidimetry, nephelometry, latex-enhanced turbidimetry or nephelometry, or solid phase immune tests. Further methods known in the art (such as gel electrophoresis, 2D gel electrophoresis, SDS polyacrylamid gel electrophoresis (SDS-PAGE), Western Blotting, and mass spectrometry), may also be used alone or in combination with labelling or other detection methods as described above.

According to some embodiments, the amount of a peptide or polypeptide may be determined as follows: (a) contacting a solid support comprising a ligand for the peptide or polypeptide as specified above with a sample comprising the peptide or polypeptide and (b) measuring the amount of the peptide or polypeptide which is bound to the support. In some exemplified embodiments, the ligand may be chosen from the group consisting of nucleic acids, peptides, polypeptides, antibodies and aptamers, may be present on a solid support in immobilized form. Materials for manufacturing solid supports are known in the art and include, for example, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier may be either soluble or insoluble, according to the disclosure. Methods for fixing/immobilizing said ligand are also known and include, but are not limited to ionic, hydrophobic, covalent interactions and the like. It is also contemplated to use "suspension arrays" as arrays according to the present disclosure (see, for example, Nolan 2002, Trends Biotechnol. 20(1):9-12). In various embodiments of suspension arrays, the carrier (for example, a microbead or microsphere) may be present in suspension. The array may consist of different microbeads or microspheres, possibly labeled, carrying different ligands. Methods of producing such arrays, for example based on solid-phase chemistry and photo-labile protective groups, are known (see for example U.S. Pat. No. 5,744,305).

The term "amount" as used herein encompasses an absolute amount of a polypeptide or peptide, the relative amount (or concentration) of the polypeptide or peptide, and any value or parameter which correlates thereto or can be derived therefrom. Such values or parameters comprise intensity signal values from all specific physical or chemical properties obtained from the said peptides by direct measurements, for example intensity values in mass spectra or NMR spectra. Moreover, encompassed are all values or parameters which are obtained by indirect measurements specified elsewhere in this description, such as response levels determined from biological read out systems in response to the peptides or intensity signals obtained from specifically bound ligands. Values correlating to the aforementioned amounts or parameters may also be obtained by all standard mathematical operations.

As used herein, the term "sample" may refer to a sample of a body fluid, a sample of separated cells, or even a sample from a tissue or an organ. Samples of body fluids may be obtained according to any known techniques and include, for example, samples of blood, plasma, serum, urine, or buccal swabs. Tissue or organ samples may be obtained from any tissue or organ, for example, such as by biopsy. Separated cells may be obtained from the body fluids or the tissues or organs by separating techniques such as centrifugation or cell sorting. According to embodiments of the instant disclosure, cell-, tissue- or organ samples are obtained from those cells, tissues, or organs which express or produce the peptides referred to herein.

The term "patient" as used in the present application may refer to a mammal, such as a human. The patient may suffer from a medical event and may present with the above described condition at an emergency department, for example. According to some embodiments, the patient may be an emergency patient, i.e., a patient whose condition requires immediate medical attention and/or intensive care. In some cases, such a patient may have been apparently healthy with respect to acute circulatory and acute ischemic events prior to the onset of an acute medical event. Thus, in some embodiments, the patient's vital functions may not have been monitored closely or even at all before arrival at the emergency department. Thus, in some embodiments, little retrospective information may be available about the cause of the life threatening condition of the patient when he presents at the emergency department. In such situations and embodiments, the method of the present disclosure, rapidly performed at the point of care, is helpful as a first indicator of the cause of the patient's condition and for guiding further (in some cases more specific) diagnostic measures.

Exemplary "further" diagnostic measures may include standard laboratory diagnostic procedures such as measuring creatinin, glucose, electrolyte, liver enzymes; total blood cell count; blood gas analysis; and imaging (such as ECG, echocardiography, computer tomography, and angiography) for example.

The term "comparing" as used herein encompasses comparing the amount of the peptide or polypeptide comprised by the sample to be analyzed with an amount of a suitable reference source specified elsewhere in this description. It is to be understood that comparing as used herein refers to a comparison of corresponding parameters or values, such as an absolute amount compared to an absolute reference amount while a concentration is compared to a reference concentration or an intensity signal obtained from a test sample is compared to the same type of intensity signal of a reference sample, for example. The comparison referred to in step (c) of the method of the present invention may be carried out manually or computer assisted, for example. For a computer assisted comparison, the value of the determined amount may be compared to values corresponding to suitable references which are stored in a database by a computer program. The computer program may further evaluate the result of the comparison, i.e. automatically provide the desired assessment in a suitable output format. Based on the comparison of the amounts determined in steps a) and b) and the reference amounts of the method of the present invention, it is possible to predict the risk of the subject of suffering of one or more of the complications referred to herein. Therefore, the reference amount may be chosen so that either a difference or a similarity in the compared amounts allows identifying those patients whose condition is caused by an acute circulatory event, by an ischemic event, by both kinds of events or by none of these events.

The term "reference amount" as used herein refers to an amount which allows diagnosing whether a patient suffered from an acute circulatory event, an ischemic event, both kinds of event or none of them. Accordingly, the reference may be derived from any of (i) a patient known to have suffered from the respective kind of event or (ii) a patient known to have not suffered from the respective event, for example. Moreover, the reference amount may define a threshold amount, whereby an amount larger than the threshold is indicative for a subject which has suffered one or both of the above mentioned events. The reference amount applicable for an individual subject may vary depending on various physiological parameters such as age, gender, or subpopulation, as well as on the means used for the determination of the polypeptide or peptide referred to herein. A suitable reference amount may be determined by the method of the present invention from a reference sample to be analyzed together, i.e. simultaneously or subsequently, with the test sample. A preferred reference amount serving as a threshold may be derived from the upper limit of normal (ULN), for example the upper limit of the physiological amount found in a population of subjects who have not suffered or are not suffering from the complications as defined above. The ULN for a given population of subjects may be determined by various known techniques. A suitable technique, for example, may be to determine the median of the population for the peptide or polypeptide amounts to be determined in the method of the present invention.

Reference amounts of a diagnostic marker (e.g., of ANP-type peptide or sFlt-1) can be established, and the level of the marker in a patient sample may be compared to the reference amount. The sensitivity and specificity of a diagnostic and/or prognostic test depends on more than just the analytical "quality" of the test, for example, they also depend on how abnormal results are identified (or characterized). The distribution of the measured amounts of the markers of the present invention, in a population of patients suffering or having suffered from a circulatory and/or ischemic complication, may be compared to the distribution of the amounts of the markers in patients without the complication(s). Statistical methods known to a person of skill in the art can be used to define a threshold amount that may be used to separate patients having suffered from one or both of the said complications and patients not having suffered from said complications. For example, the calculation of Receiver Operating Characteristic curves, or "ROC" curves may be used for this purpose. ROC-curves are typically calculated by plotting the value of a variable versus its relative frequency in "normal" and "disease" populations. For example, with any particular marker, a distribution of marker levels for subjects with and without a disease may (and even likely will) overlap. Under such conditions, a test does not absolutely distinguish normal from disease with 100% accuracy, and the area of overlap may indicate where the test cannot distinguish normal from disease. A threshold may be selected, above which (or below which, depending on how a marker changes with the disease) the test is considered to be abnormal and below which the test is considered to be normal. The area under the ROC curve is a measure of the probability that the perceived measurement will allow correct identification of a condition. ROC curves can be used even when test results do not necessarily give an accurate number. As long as one can rank results, one can create an ROC curve. For example, results of a test on "disease" samples might be ranked according to degree (say 1=low, 2=normal, and 3=high). This ranking can be correlated to results in the "normal" population, and a ROC curve created. These methods are known in the art, for example, see Hanley et al, Radiology 143: 29-36 (1982).

In certain embodiments, markers (for example, ANP-type peptide and sFlt-1) are selected to exhibit at least about 70% sensitivity and in some case at least about 80% sensitivity, at least about 85% sensitivity, at least about 90% sensitivity, and even at least about 95% sensitivity, combined with at least about 70% specificity, at least about 80% specificity, at least about 85% specificity, at least about 90% specificity, or even at least about 95% specificity. In exemplary embodiments, both the sensitivity and specificity are at least about 75%, at least about 80%, at least about 85%, at least about 90%, and even at least about 95%. The term "about" in this context refers to +/−5% of a given measurement.

The reference amount for NT-proANP comprises about 1000 pg/ml, about 2000 pg/ml, about 2500 pg/ml, about 3000 pg/ml, about 4000 pg/ml or about 5000 pg/ml. According to some exemplified embodiments, reference amount for NT-proANP comprises about 2500 pg/ml. According to such embodiments, amounts larger than this amount are indicative of a patient having suffered from a circulatory complication.

If the circulatory complication is an arrhythmia, the reference amount for NT-proANP may comprise about 1000 pg/ml, about 2000 pg/ml, about 2500 pg/ml, about 3000 pg/ml, about 4000 pg/ml or about 5000 pg/ml, for example. According to some exemplified embodiments the reference amount for NT-proANP comprises about 2500 pg/ml. If the circulatory complication is tachycardia, the reference amount may comprise about 1000 pg/ml, about 2000 pg/ml, about 2500 pg/ml, about 3000 pg/ml, about 4000 pg/ml or about 5000 pg/ml. According to some exemplified embodiments, the reference amount comprises about 2500 pg/ml.

The reference amount for sFlt-1 comprises about 100 pg/ml, about 200 pg/ml, about 300 pg/ml, about 400 pg/ml, about 500 pg/ml, about 750 pg/ml or about 1000 pg/ml. According to some exemplified embodiments, the reference amount comprises about 500 pg/ml. According to such embodiments, amounts larger than this amount are indicative of a patient having suffered an ischemic complication.

The term "about" is meant to indicate +/−30% of the indicated amount. In some embodiments of the instant disclosure, the term "about" is indicative of +/−20% of the indicated amount or even +/−10% of the indicated amount or even +/−5% of the indicated amount.

Increased levels of sFlt-1 and the ANP-type peptide are indicative of a combined circulatory and ischemic complication. The reference amounts cited above for sFlt-1 and the ANP-type peptide also apply for combined circulatory and ischemic complications, including those for particular circulatory complications like arrhythmia and tachycardia.

In view of the above explanations and examples, a reference value for an ANP-type peptide other than NT-proANP, may be determined allowing for diagnosis of a pathophysiological cause of an acute medical event in an emergency patient is a circulatory complication.

Embodiments of the method of the present invention allows for a rapid diagnosis and guidance for further examination/diagnosis aiming at establishing the exact cause or causes underlying the pathophysiological state of patients suffering from an acute medical event or aiming at establishing the disease or condition which the patient suffers from. For example, by indicating a cause underlying an organ failure the method is able to guide the further diagnosis. Thus, for example, it is possible to exclude certain diseases by differential diagnosis. The reduced time for diagnosis enables a more rapid onset of causal treatment and, thus, reduces the suffering of the patient, may prevent a further deterioration of the patient's condition or even death, for example. The method of the present invention also may be performed at the bed side, thus leading the physician early and quickly to the other required diagnostic measures.

For example, embodiments of methods of the present invention may also indicate not only the cause, but also the extent or severity of a circulatory or ischemic complication. Complications of greater extent or severity may be associated with higher amounts of the ANP-type peptide and/or sFlt-1 as compared to complications of lesser extent or severity. For example, a reference amount may be determined in a patient with a complication of known extent or severity. Comparison of a sample from a patient suffering from or having suffered from a complication of unknown extent or severity to a reference amount derived from a patient or collective of patients having suffered a complication of known severity makes it possible to establish the extent or severity of said patient's complication quickly. For example, amounts of the ANP-type peptide and/or sFlt-1 that are higher than the reference amount may indicate a more severe or extended complication. Criteria for the extent and/or severity of a condition, include its duration (e.g., a longer period of cardiac arrhythmia), or the intensity of the complication (e.g., the amount of ischemic tissue).

Furthermore, embodiments of the present invention may relate to a device for, or adapted for, assessing (including rapidly assessing) if the pathophysiological cause of an acute medical event in an emergency patient is a circulatory and/or an ischemic complication. Exemplary embodiments may comprise:

a) means for determining the amount of an ANP-type peptide in a sample of a patient;
b) means for determining the amount of sFlt-1 in a sample from a patient;
c) means for comparing the measured amounts of the ANP-type peptide and sFlt-1 to reference amounts; and
d) means for establishing a diagnosis based on the results of the comparison.

The term "device" as used herein relates to a system of means comprising at least the aforementioned means operatively linked to each other as to allow the prediction. Exemplary means for determining the amounts of an ANP-type peptide and sFlt-1, and means for carrying out the comparison are disclosed above in connection with the method of the invention. Exemplary methods for linking the means in an operating manner will depend on the type of means included in the device. For example, where means for automatically determining the amount of the peptides are applied, the data obtained by said automatically operating means can be processed by a computer program, for example, in order to obtain the desired results. The means may comprise a single device in such a case, for example. Said device may accordingly include an analyzing unit for the measurement of the amount of the peptides or polypeptides in an applied sample and a computer unit for processing the resulting data for the evaluation. Alternatively, where means such as test strips are used for determining the amount of the peptides or polypeptides, the means for comparison may comprise control strips or tables allocating the determined amount to a reference amount. The test strips may be coupled to a ligand which specifically binds to the peptides or polypeptides referred to herein, for example. The strip or device may comprise means for detection of the binding of said peptides or polypeptides to the said ligand. Exemplary means for detection are disclosed in connection with embodiments relating to the method of the invention above. In such a case, the means are operatively linked in that the user of the system brings together the result of the determination of the amount and the diagnostic or prognostic value thereof due to the instructions and interpretations given in a manual. The means may appear as separate devices in such an embodiment and may be packaged together as a kit. A person of skill in the art will understand how to link the means. Preferred devices are those which can be applied without the particular knowledge of a specialized clinician (for example, test strips or electronic devices which merely require loading with a sample). The results may be given as output of raw data which need interpretation by the clinician as processed information (i.e. evaluated raw data, the interpretation of which does not require a clinician). Further exemplary devices comprise the analyzing units/devices (such as, biosensors, arrays, solid supports coupled to ligands specifically recognizing the peptide, Plasmon surface resonance devices, NMR spectrometers, mass-spectrometers, etc.) and/or evaluation units/devices referred to above in accordance with methods described and disclosed herein.

Additionally, as disclosed above, according to some embodiments of the present disclosure, a kit for rapidly assessing if the pathophysiological cause of an acute medical event in an emergency patient is a circulatory and/or an ischemic complication is provided. Such embodiments may comprise:

a) means for determining the amount of a ANP-type peptide in a sample of a patient;
b) means for determining the amount of sFlt-1 in a sample from a patient;

c) means for comparing the measured amounts of the ANP-type peptide and sFlt-1 to reference amounts; and
d) means for establishing a diagnosis based on the results of the comparison.

As used herein, the term "kit" may refer to a collection of the aforementioned means. For example, such means may be provided within a separate container or within a single container. The container may also comprise instructions for carrying out the methods disclosed and described herein.

According to other embodiments of the instant disclosure, methods for diagnosis of a vascular disease with atherosclerotic etiology are provided. Such embodiments may comprise the steps of:
a) determining the amount of an ANP-type peptide in a sample of a patient;
b) determining the amount of sFlt-1 in a sample from a patient;
c) comparing the amounts measured in steps a) and b) to reference amounts; and
d) establishing a diagnosis based on the results of c).

According to some embodiments, the instant disclosure relates to a method for diagnosing whether a diabetes patient is suffering from a cardiovascular complication or is at risk of suffering from a cardiovascular complication. Such embodiments may comprise the steps of:
a) measuring, preferably in vitro, the level(s) of at least one cardiac hormone (e.g. NT-proBNP) in a sample from the patient; and
b) diagnosing the cardiovascular complication or the risk of suffering from cardiovascular complication by comparing the measured level(s) to known level(s) associated with the cardiovascular complication or the risk.

Moreover, a method for diagnosing whether a diabetes patient is suffering from a microangiopathy or is at risk of suffering from a microangiopathy is disclosed herein. According to some embodiments, this method comprises the steps of:
a) measuring in vitro the level(s) of PLGF or PLGF-1 variant in blood serum, blood or blood plasma sample from the patient; and
b) diagnosing microangiopathy or the risk of suffering from microangiopathy by comparing the measured level(s) to known level(s) associated with microangiopathy or the risk.

The following examples, sequence listing, and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure.

EXAMPLES

Example 1

In 403 patients (median age: 52.4 years) with life threatening conditions which required intensive care sFlt-1 and NT-proANP were determined within 4 hours after hospitalization. At the time of sampling all patients were mechanically ventilated. Their circulation was stable.

NT-proANP was determined with the proANP ELISA assay (BI-20892) obtained from Biomedica, Vienna, Austria. This sandwich assay comprises a polyclonal sheep NT-proANP specific antibody bound to a microtiterstrip. The sample is added to the microtiterstrip so that the proANP can bind to the antibody. After binding of the proANP to the first antibody a second proANP specific antibody is added to the vessel. This second antibody is conjugated with horseradish peroxidase (HRP). After incubation the unbound enzyme-conjugated antibody is removed by washing the microtiterstrip. Finally, tetramethylbenzidine (TMB) is added as a substrate for the HRP. The more proANP the sample contains, the more conjugated antibody binds. Thus, the total activity of HRP present in the vessel depends on the amount of proANP in the sample and the initial rate of TMB converted is a measure for the amount of NT-proANP in the sample.

sFlt-1 was determined with a sFlt-1 immunoassay to be used with the Elecsys and COBAS analyzers from Roche Diagnostics, Mannheim, Germany. The assay is based on the sandwich principle and comprises two monoclonal sFlt-1 specific antibodies. The first of these is biotinylated and the second one is labelled with a Tris(2,2'-bipyridyl)ruthenium (II)-complex. In a first incubation step both antibodies are incubated with the sample. A sandwich complex comprising sFlt-1 and the two different antibodies is formed. In a next incubation step streptavidin-coated beads are added to this complex. The beads bind to the sandwich complexes. The reaction mixture is then aspirated into a measuring cell where the beads are magnetically captured on the surface of an electrode. The application of a voltage then induces a chemiluminescent emission from the ruthenium complex which is measured by a photomultiplier. The amount of light is dependent on the amount of sandwich complexes on the electrode.

Tachycardia was determined by electrocardiography or by measuring the pulse of the patient for at least 30 seconds.

TABLE 1

Circulatory events.

| NT-proANP [pg/ml] | N* | Patients with arrhythmia§ | [%] | Patients with tachycardia** | [%] |
|---|---|---|---|---|---|
| <1000 | 64 | 0 | 0.0 | 12 | 18.8 |
| 1000 to 2500 | 204 | 16 | 0.8 | 101 | 49.5 |
| 2500 to 5000 | 97 | 32 | 33.0 | 59 | 60.8 |
| 5000 to 10,000 | 35 | 21 | 60.0 | 28 | 80.0 |
| >10,000 | 3 | 1 | 33.3 | 3 | 100.0 |

*Total number of patients
**Tachycardia was diagnosed if the patient exhibited a pulse rate of >120 bpm.
§Arrhythmia was defined as absolute arrhythmia or more than 10 extra heart beats per minute

TABLE 2

Proportion of patients with ischemic events (systolic BP <80 mmHg).

| sFlt1 [pg/ml] | N* | Ischemic events** | [%] |
|---|---|---|---|
| <100 | 229 | 2 | 0.0 |
| 100 to 500 | 140 | 11 | 0.8 |
| 500 to 1000 | 4 | 1 | 25.0 |
| 1000 to 5000 | 9 | 6 | 66.7 |
| >5000 | 21 | 13 | 61.9 |

*Total number of patients
**Number of patients.

Patients were considered to suffer from an ischemic event if the following criteria were met: organ specific pain, reduced pulse in the affected area and paleness of the skin.

Table 1 shows that with increasing amounts of NT-proANP the proportion of patients with circulatory events increased. More than 33% of patients with NT-proANP levels above about 2500 pg/ml had suffered before sampling or still suffered at the time of sampling from arrhythmia and more than 60% of the patients with NT-proANP levels above 2500 pg/ml had suffered before sampling or still suffered at the time of sampling from tachycardia. Thus, by measuring the NT-proANP level in the emergency patients, circulatory complications, as exemplified by arrhythmia and tachycardia may be reliably diagnosed. To the surprise of the inventors, such diagnosis may be accomplished even within 4 h after hospitalization.

Table 2 shows the prevalence of ischemic events. More than 25% of the patients with sFlt-1 levels above about 500 pg/ml had suffered before sampling, or still suffered at the time of sampling, from a systolic blood pressure below 80 mmHg.

In view of the above, measuring the sFlt-1 level in the emergency patients allows for safely and rapidly diagnosing ischemic complications.

Each of the two markers sFlt-1 and NT-proANP (or another ANP-type peptide) provides for a statistically independent diagnostic measure. By combining the measurement of sFlt-1 and NT-proANP (or another ANP-type peptide) into one diagnostic test, a physician may readily and quickly determine the pathophysiological cause of an acute medical event in an emergency patient, such as if the given emergency patient suffers from a circulatory and/or an ischemic complication.

ILLUSTRATIVE EMBODIMENTS

1. A method for rapidly diagnosing if an acute medical event in an emergency patient is associated with a circulatory and/or an ischemic complication, comprising the steps of
    a) determining the amount of an ANP-type peptide in a sample of a patient;
    b) determining the amount of sFlt-1 in a sample from a patient;
    c) comparing the amounts measured in steps a) and b) to reference amounts; and establishing a diagnosis based on the results of c),
    d) establishing a diagnosis based on the results of c), wherein an increased level of the ANP-type peptide relative to the reference amount is indicative of a circulatory complication and wherein an increased level of sFlt-1 relative to the reference amount is indicative of an ischemic complication,
    wherein the circulatory complication is caused by cardiac arrhythmia, and
    wherein the ischemic complication is characterized by a systolic blood pressure of less than 80 mmHg.
2. The method of 1, wherein increased levels of sFlt-1 and the ANP-type peptide relative to the reference amounts are indicative of a combined circulatory and ischemic complication.
3. The method of 1, wherein the acute medical event is heart failure, lung failure or renal failure.
4. The method of 2, wherein the ischemic complication occurs in the spleen, in the heart, in the kidney, in the bowel or in the limbs.
5. The method of 1, wherein the ANP-type peptide is NT-proANP.
6. The method of 5, wherein the reference amount for NT-proANP is about 2500 pg/ml.
7. The method of 1, wherein the reference amount for sFlt-1 is about 500 pg/ml.
8. A device for rapidly diagnosing if an acute medical event in an emergency patient is associated with a circulatory and/or an ischemic complication, comprising
    a) analyzing unit for determining the amount of an ANP-type peptide in a sample of a patient;
    b) analyzing unit for determining the amount of sFlt-1 in a sample from a patient;
    c) computer unit for comparing the measured amounts of the ANP-type peptide and sFlt-1 to reference amounts; and
    d) computer unit for establishing a diagnosis based on the results of the comparison, wherein an increased level of the ANP-type peptide relative to the reference amount is indicative of a circulatory complication and wherein an increased level of sFlt-1 relative to the reference amount is indicative of an ischemic complication, and
    wherein the circulatory complication is caused by cardiac arrhythmia, and
    wherein the ischemic complication is characterized by a systolic blood pressure of less than 80 mmHg.
9. The device of 8, wherein the ANP-type peptide is proANP.
10. A kit for rapidly diagnosing if an acute medical event in an emergency patient is associated with a circulatory and/or an ischemic complication, said kit comprising instructions for carrying out the diagnosis, and further comprising
    a) analyzing unit for determining the amount of an ANP-type peptide in a sample of a patient;
    b) analyzing unit for determining the amount of sFlt-1 in a sample from a patient;
    c) computer unit for comparing the measured amounts of the ANP-type peptide and sFlt-1 to reference amounts; and
    d) computer unit for establishing a diagnosis based on the results of the comparison, wherein an increased level of the ANP-type peptide relative to the reference amount is indicative of a circulatory complication and wherein an increased level of sFlt-1 relative to the reference amount is indicative of an ischemic complication
    wherein the circulatory complication is caused by cardiac arrhythmia, and
    wherein the ischemic complication is characterized by a systolic blood pressure of less than 80 mmHg.
11. The kit of 9, wherein the ANP-type peptide p-reference is proANP.

All publications, patents and applications are hereby incorporated by reference in their entirety to the same extent as if each such reference was specifically and individually indicated to be incorporated by reference in its entirety.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. A method for diagnosing a circulatory complication comprising cardiac arrhythmia and/or an ischemic complication comprising systolic blood pressure of less than 80 mmHg in a subject comprising:
    a) obtaining a serum or plasma sample from a subject suffering from an acute medical event, b) contacting, in vitro, a portion of a serum or plasma sample from said subject with an antibody immunoreactive for an NT-proANP peptide;
c) contacting, in vitro, a portion of the same serum or plasma sample with two antibodies immunoreactive for different portions of a sFlt-1 peptide, wherein the first antibody has one of a biotin and a streptavidin linked thereto and wherein the second antibody has a Tris (2,2'-bipyridyl) ruthenium (H)-complex linked thereto;
d) determining the amounts of NT-proANP peptide and sFlt-1 peptide in said sample based on the contacting steps of b) and c);
e) comparing the amounts of the NT-proANP peptide and sFlt-1 peptide determined in step d) with reference amounts for NT-proANP peptide and sFlt-1 peptide, respectively; and
f) diagnosing a circulatory complication comprising cardiac arrhythmia if the amount of NT-proANP-type peptide determined in step d) is greater than the reference amount of about 2500 pg/ml for NT-proANP peptide, and
diagnosing an ischemic complication comprising systolic blood pressure of less than 80 mmHg if the amount of sFlt-1 peptide determined in step d) is greater than the reference amount of about 500 pg/ml for sFlt-1 peptide.

2. The method of claim 1, wherein the antibody in step b) is bound to a microtiterstrip.

3. The method of claim 1, where step b) requires contacting said sample with two antibodies immunoreactive for different portions of the NT-proANP peptide,
wherein the first antibody is a polyclonal sheep NT-proANP-specific antibody and the second antibody is conjugated with horseradish peroxidase (HRP).

* * * * *